US012569468B2

(12) United States Patent
Zhang et al.

(10) Patent No.: US 12,569,468 B2
(45) Date of Patent: Mar. 10, 2026

(54) USE OF PALOVAROTENE IN TREATMENT AGAINST HBV VIRUS

(71) Applicants: YANG SHENG TANG COMPANY, LTD., Zhejiang (CN); XIAMEN UNIVERSITY, Fujian (CN)

(72) Inventors: Tianying Zhang, Fujian (CN); Jiali Cao, Fujian (CN); Tianshu Shi, Fujian (CN); Jian Ma, Fujian (CN); Shaojuan Wang, Fujian (CN); Quan Yuan, Fujian (CN); Jun Zhang, Fujian (CN); Ningshao Xia, Fujian (CN)

(73) Assignees: Yang Sheng Tang Company, Ltd., Zhejiang (CN); Xiamen University, Fujian (CN)

( * ) Notice: Subject to any disclaimer, the term of this patent is extended or adjusted under 35 U.S.C. 154(b) by 642 days.

(21) Appl. No.: 18/001,167

(22) PCT Filed: Jun. 1, 2021

(86) PCT No.: PCT/CN2021/097626

§ 371 (c)(1),
(2) Date: Dec. 8, 2022

(87) PCT Pub. No.: WO2021/249240

PCT Pub. Date: Dec. 16, 2021

(65) Prior Publication Data

US 2023/0218576 A1 Jul. 13, 2023

(30) Foreign Application Priority Data

Jun. 11, 2020 (CN) ......................... 202010531845.9

(51) Int. Cl.
*A61K 31/415* (2006.01)
*A61P 31/20* (2006.01)

(52) U.S. Cl.
CPC ............ *A61K 31/415* (2013.01); *A61P 31/20* (2018.01)

(58) Field of Classification Search
CPC .............................. A61K 31/415; A61P 31/20
See application file for complete search history.

(56) References Cited

U.S. PATENT DOCUMENTS

| | | | | |
|---|---|---|---|---|
| 2002/0082265 | A1* | 6/2002 | Lapierre | C07D 277/30 514/354 |
| 2017/0216430 | A1 | 8/2017 | Shishido et al. | |

FOREIGN PATENT DOCUMENTS

| | | | |
|---|---|---|---|
| CN | 109562099 | A | 4/2019 |
| CN | 110381939 | A | 10/2019 |
| JP | 2019-094262 | A | 6/2019 |
| JP | 2019-517557 | A | 6/2019 |
| WO | 2017/210792 | A1 | 12/2017 |
| WO | 2018/090137 | A1 | 5/2018 |
| WO | 2018/195450 | A1 | 10/2018 |
| WO | 2019/079339 | A1 | 4/2019 |

OTHER PUBLICATIONS

Mawson & Steele, Possible Role of Retinoids in Hepatitis B Virus-Associated Liver Damage, 226(8) Exp. Biol. Med. 734-739 (2001) (Year: 2001).*
English Translation of International Search Report issued in PCT/CN2021/097626, mailed Sep. 7, 2021.
Birkus et al., "Anti-HBV activity of retinoid drugs in vitro versus in vivo" Antiviral Res. 169:104538 (2019).
Li et al., "Identification of Retinoic Acid Receptor Agonists as Potent Hepatitis B Virus Inhibitors via a Drug Repurposing Screen" Antimicrobial Agents and Chemotherapy 62(12):e00465-18 (2018).

* cited by examiner

*Primary Examiner* — Timothy R Rozof
(74) *Attorney, Agent, or Firm* — Medler Ferro Woodhouse and Mills PLLC

(57) ABSTRACT

The present application relates to the field of antiviral treatment of hepatitis B, and specifically relates to the use of a compound represented by formula I in treatment against HBV virus.

I

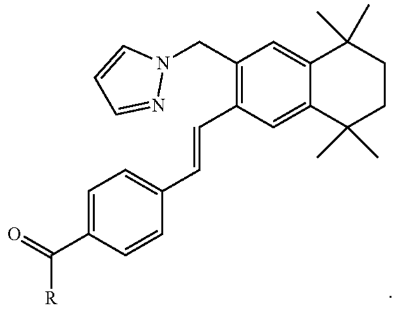

20 Claims, 8 Drawing Sheets palovarotene

USE OF PALOVAROTENE IN TREATMENT AGAINST HBV VIRUS

The present application is based on and claims the benefit of priority from Chinese application No. 202010531845.9, filed on Jun. 11, 2020, the disclosure of which is incorporated herein by reference in its entirety.

TECHNICAL FIELD

The present application relates to the field of antiviral treatment of hepatitis B, and specifically to the use of a small molecule drug (e.g., Palovarotene) represented by Formula I in anti-HBV treatment,

I

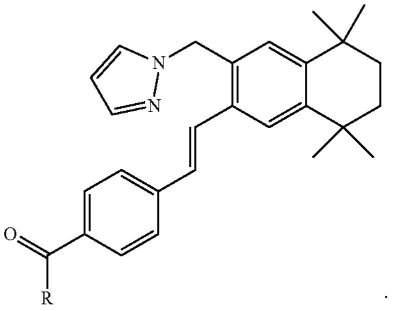

.

BACKGROUND ART

Viral hepatitis B, abbreviated as hepatitis B, is a disease caused by the body infection of hepatitis B virus (HBV). The World Health Organization estimates that 3.5% of the world's population (257 million) has been infected with the hepatitis B virus, with approximately 5 million new infections each year. Worldwide, more than 800,000 people die every year from various liver diseases caused by HBV infection, including chronic active hepatitis, liver cirrhosis, and hepatocellular carcinoma. China is an intermediate or high endemic area of hepatitis B virus infection. Although the widespread vaccination of hepatitis B vaccine has effectively reduced the number of new HBV infections, it is estimated that there are still more than 70 million people with chronic HBV infection in China, in which chronic hepatitis B (CHB) patients amount to 20-30 million, about 500 thousand people die from HBV infection each year, and about 500 thousand to 1 million new cases of hepatitis B are diagnosed each year. Hepatitis B virus infection has seriously endangered human health and brought long-term disease burden, and is one of the most prominent public health problems in China at this stage.

At present, there are two main types of treatment drugs for chronic hepatitis B patients: nucleos(t)ide analogue (NAs) or interferon α (IFNα), among which interferon α is pegylated interferon α (PEGIFNα). The EU-approved NAs for HBV treatment include Adefovir (ADV), Entecavir (ETV), Lamivudine (LAM), Telbivudine (TBV), Tenofovir (TDF) and Tenofovir averamide (TAF). These drugs have been shown to inhibit viral replication, delay or suppress disease progression, and reduce the risk of developing cirrhosis and liver cancer.

However, the current clinical use of PEGIFNa/NAs drugs and their optimized combination is still difficult to achieve a high proportion of "clinical cure" (clearance of serum hepatitis B surface antigen (HBsAg); clearance of hepatitis B e antigen (HBeAg) which is an important indicator for virus replication and patients' antiviral treatment prognosis; with or without positive hepatitis B surface antibody). Existing studies believe that although PEGIFNa/NAs can prevent virus replication, they cannot effectively reduce HBsAg level, nor can they directly affect covalently closed circular DNA (cccDNA, which is considered to be the transcription and replication template of HBV) that stably exists in the liver, thereby resulting in virological rebound soon after drug withdrawal in most patients even in the state where viral replication is controlled for a long time by treatment.

The development of an antiviral drug that can effectively reduce the levels of serum HBsAg, HBeAg, HBV DNA and cccDNA in patients with chronic hepatitis B has urgent practical significance for the antiviral treatment and prognosis of patients with chronic hepatitis B.

CONTENTS OF THE INVENTION

The inventors surprisingly found in their research that Palovarotene (structural formula shown in FIG. 1) treatment can significantly reduce HBsAg and HBeAg levels in the cell culture supernatant, and intracellular HBV DNA and cccDNA levels in vitro research models (infection model: HepG2-hNTCP 2B1, HepaRG M14a, PHH; replication model: HepAD38). Based on the above findings, the present application has been completed.

The present application relates to use of a compound represented by Formula I, a stereoisomer, a solvate, a pharmaceutically acceptable salt, a hydrate or a solvate of the pharmaceutically acceptable salt, its pharmaceutically acceptable ester, or various pharmaceutically acceptable modifications thereof,

I

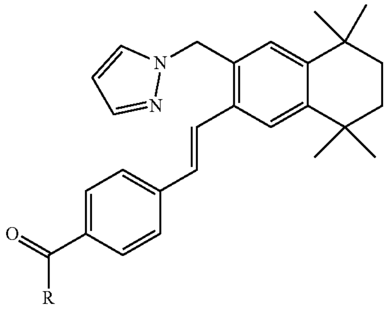

wherein R is hydroxyl, amino, $C_{1-6}$ alkyl-amino-, di($C_{1-6}$ alkyl)-amino-, $C_{1-6}$ alkoxy, $C_{1-6}$ haloalkoxy, $C_{1-6}$ alkyl, $C_{1-6}$ haloalkyl, $C_3$-$_6$ cycloalkyl, $C_3$-$_6$ cycloalkoxy, phenoxy or benzyloxy.

Specifically, the present application relates to use of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof in the manufacture of a product for anti-HBV treatment.

The present application also relates to use of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof in the manufacture of a product as an HBV inhibitor.

The present application also relates to use of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof in the manufacture of a product for inhibiting the replication or reproduction of HBV in a cell (e.g., a cell of mammal).

The present application also relates to use of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof in the manufacture of a product for the treatment and/or prevention of a disease or infection caused by HBV.

The present application also relates to use of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof in the manufacture of a product for the clearance of HBV in a cell (e.g., a cell of mammal).

The present application also relates to a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof, for use in the anti-HBV treatment.

The present application also relates to a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof, for use as an HBV inhibitor.

The present application also relates to a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof, for use in inhibiting the replication or reproduction of HBV in a cell (e.g., a cell of mammal).

The present application also relates to a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof, for use in the treatment and/or prevention of a disease or infection caused by HBV.

The present application also relates to a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof, for use in the clearance of HBV in a cell (e.g., a cell of mammal).

The present application relates to a method for the anti-HBV treatment, comprising administering to a subject in need thereof a therapeutically effective amount of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof.

The present application also relates to a method for inhibiting the replication or reproduction of HBV in a cell (e.g. cell of mammal), comprising administering to a subject in need thereof an effective amount of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof.

The present application also relates to a method for the treatment and/or prevention of a disease or infection caused by HBV, comprising administering to a subject in need thereof a therapeutically and/or prophylactically effective amount of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof.

The present application also relates to a method for the clearance of HBV in a cell (e.g., a cell of mammal), comprising administering to a subject in need thereof an effective amount of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof.

The present application also relates to a composition for anti-HBV treatment, which comprises a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof.

The present application also relates to a composition for inhibiting the replication or reproduction of HBV in a cell (e.g., a cell of mammal), which comprises a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof.

The present application also relates to a composition for the treatment and/or prevention of a disease or infection caused by HBV, which comprises a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof.

The present application also relates to a composition for the clearance of HBV in a cell (e.g., a cell of mammal), which comprises a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof.

According to some embodiments of the present application, the disease caused by HBV described in the present application is viral hepatitis B.

According to some embodiments of the present application, the disease caused by HBV described in the present application is hepatitis B-related liver cirrhosis or primary liver cancer.

According to some embodiments of the present application, the viral hepatitis B described in the present application is chronic viral hepatitis B, acute viral hepatitis B, or chronic active hepatitis.

According to some embodiments of the present application, the product described in the present application is a pharmaceutical product.

According to some embodiments of the present application, the pharmaceutical composition described in the present application further comprises a pharmaceutically acceptable carrier or excipient.

According to some embodiments of the present application, the pharmaceutical composition described in the present application is a solid preparation (e.g., tablet, capsule, pill, granule, powder), an injection, an external preparation, a spray, a liquid preparation, or a compound preparation.

According to some embodiments of the present application, the pharmaceutical compositions described in the present application may be administered orally, by injection, by implantation, by external application, by spraying, or by inhalation.

According to some embodiments of the present application, in the compound represented by Formula I described in the present application, R is hydroxy, amino, methyl, ethyl, n-propyl, isopropyl, n-butyl, isobutyl, sec-butyl, tert-butyl, $C_5$ straight or branched alkyl, $C_6$ straight or branched alkyl, methoxy, ethoxy, n-propoxy, isopropoxy, n-butoxy, isobutoxy, tert-butoxy, pentyloxy, hexyloxy, methylamino, ethylamino, propylamino, butylamino, dimethylamino, diethylamino, dipropylamino, dibutylamino, cyclopropyl, cyclobutyl, cyclopentyl, cyclohexyl, cyclopropoxy, cyclobutoxy, cyclopentyloxy, cyclohexyloxy, phenoxy, benzyloxy, chloromethyl, chloroethyl, dichloroethyl, trifluoromethyl, difluoromethyl, monofluoromethyl, chloromethoxy, chloroethoxy, dichloroethoxy, trifluoromethoxy, difluoromethoxy, or monofluoromethoxy.

According to some embodiments of the present application, in the compound represented by Formula I described in the present application, R is hydroxyl, and in this case, the compound is Palovarotene.

According to some embodiments of the present application, in the compound represented by Formula I described in the present application, R is amino, methylamino, ethylamino, propylamino, butylamino, dimethylamino, diethylamino, dipropylamino or dibutylamino.

According to some embodiments of the present application, in the compound represented by Formula I described in the present application, R is amino.

According to some embodiments of the present application, in the compound represented by Formula I described in the present application, R is methylamino or ethylamino.

According to some embodiments of the present application, in the compound represented by Formula I described in the present application, R is dimethylamino or diethylamino.

According to some embodiments of the present application, in the compound represented by Formula I described in the present application, R is methoxy, ethoxy, n-propoxy, isopropoxy, n-butoxy, isobutoxy, tert-butoxy, pentyloxy or hexyloxy.

According to some embodiments of the present application, in the compound represented by Formula I described in the present application, R is methoxy.

According to some embodiments of the present application, in the compound represented by Formula I described in the present application, R is ethoxy.

According to some embodiments of the present application, in the compound represented by Formula I described in the present application, R is n-propoxy.

According to some embodiments of the present application, in the compound represented by Formula I described in the present application, R is isopropoxy.

According to some embodiments of the present application, in the compound represented by Formula I described in the present application, R is n-butoxy.

According to some embodiments of the present application, in the compound represented by Formula I described in the present application, R is isobutoxy.

According to some embodiments of the present application, in the compound represented by Formula I described in the present application, R is tert-butoxy.

According to some embodiments of the present application, in the compound represented by Formula I described in the present application, R is pentyloxy.

According to some embodiments of the present application, in the compound represented by Formula I described in the present application, R is hexyloxy.

According to some embodiments of the present application, in the compound represented by Formula I described in the present application, R is cyclopropoxy, cyclobutoxy, cyclopentyloxy or cyclohexyloxy.

According to some embodiments of the present application, in the compound represented by Formula I described in the present application, R is cyclopropoxy or cyclobutoxy.

According to some embodiments of the present application, in the compound represented by Formula I described in the present application, R is phenoxy or benzyloxy.

According to some embodiments of the present application, in the compound represented by Formula I described in the present application, R is methyl, ethyl, n-propyl, isopropyl, n-butyl, isobutyl, sec-butyl, tert-butyl, $C_5$ straight or branched alkyl, or $C_6$ straight or branched alkyl.

According to some embodiments of the present application, in the compound represented by Formula I described in the present application, R is methyl or ethyl.

According to some embodiments of the present application, in the compound represented by Formula I described in the present application, R is n-propyl.

According to some embodiments of the present application, in the compound represented by Formula I described in the present application, R is cyclopropyl, cyclobutyl, cyclopentyl or cyclohexyl.

According to some embodiments of the present application, in the compound represented by Formula I described in the present application, R is chloromethyl, chloroethyl, dichloroethyl, trifluoromethyl, difluoromethyl or monofluoromethyl.

According to some embodiments of the present application, in the compound represented by Formula I described in the present application, R is chloromethyl or chloroethyl.

According to some embodiments of the present application, in the compound represented by Formula I described in the present application, R is trifluoromethyl, difluoromethyl or monofluoromethyl.

According to some embodiments of the present application, in the compound represented by Formula I described in the present application, R is chloromethoxy, chloroethoxy, dichloroethoxy, trifluoromethoxy, difluoromethoxy or monofluoromethoxy.

According to some embodiments of the present application, in the compound represented by Formula I described in the present application, R is chloromethoxy or chloroethoxy.

According to some embodiments of the present application, in the compound represented by Formula I described in the present application, R is trifluoromethoxy, difluoromethoxy or monofluoromethoxy.

According to some embodiments of the present application, the pharmaceutically acceptable salt described in the present application includes inorganic or organic acid salt, as well as inorganic or organic base salt. For example, the pharmaceutically acceptable salt includes but is not limited to: the compound's alkali metal salt, including sodium salt, potassium salt and lithium salt; alkaline earth metal salt, including calcium salt and magnesium salt; metal salt, including aluminum salt, iron salt, zinc salt, copper salt, nickel salt and cobalt salt; amine salt, including meglumine salt, ammonium salt, tert-octylamine salt, dibenzylamine salt, morpholine salt, glucosamine salt, phenylglycine alkyl ester salt, monoethanolamine salt, diethanolamine salt, triethanolamine salt, N-methyl-D-glucamine salt, ethylenediamine salt, N-methylglucamine salt, guanidine salt, diethylamine salt, triethylamine salt, bicyclohexylamine salt, N,N'-dibenzylethylenediamine salt, chloroprocaine salt, procaine salt, diethanolamine salt, N-benzyl-N-phenethylamine salt, piperazine salt, tetramethylammonium salt and tris (hydroxymethyl)aminomethane salt.

According to some embodiments of the present application, when there is a carboxyl group in the compound represented by Formula I described in the present application, it may form a pharmaceutically acceptable ester with an alcohol, and the pharmaceutically acceptable ester includes $C_1$-$_6$ alkyl ester such as methyl ester, ethyl ester, propyl ester, isopropyl ester, butyl ester, sec-butyl ester, tert-butyl ester, pentyl ester, and hexyl ester; $C_3$-$_6$ cycloalkyl ester such as cyclopentyl ester and cyclohexyl ester; $C_6$-$_{10}$ aryl ester such as phenyl ester and naphthyl ester; $C_6$-$_{10}$ aryl-$C_1$-$_6$ alkyl ester such as benzyl ester, phenylethyl ester, α-methylbenzyl ester, 3-phenylpropyl ester, 4-phenylbutyl ester, 6-phenylhexyl ester, diphenylmethyl ester and triphenylmethyl ester; or ester that may be hydrolyzed in vivo, such as (5-methyl-2-oxo-1,3-dioxol-4-yl)methyl ester, (pivaloyloxy)methyl ester, benzofuranonyl ester, [(isopropoxycarbonyl)oxy]methyl ester, [(cyclohexyloxycarbonyl)oxy]methyl ester, and 1-[(cyclohexyloxycarbonyl)oxy]ethyl ester.

The carrier described in the present application includes, but is not limited to: ion exchanger, aluminum oxide, aluminum stearate, lecithin, serum protein such as human albumin, buffer substance such as phosphate, glycerol, sorbic acid, potassium sorbate, partial glyceride mixture of saturate plant fatty acid, water, salt or electrolyte such as protamine sulfate, disodium hydrogen phosphate, potassium hydrogen phosphate, sodium chloride, zinc salt, colloidal silica, magnesium trisilicate, polyvinylpyrrolidone, cellulose material, polyethylene glycol, sodium carboxymethylcellulose, polyacrylate, beeswax, wool fat.

The term "excipient" as used in the present application refers to an additive besides main active ingredient in the pharmaceutical preparation. It is stable in nature, has no incompatibility with the main active ingredient, does not produce side effects, does not affect the efficacy, is not easy to deform, crack, mildew or worm-eaten at room temperature, is harmless to human body, has no physiological effect, does not produce chemical or physical interaction with the main active ingredient, does not affect the content determination of the main active ingredient, and so on. Examples include binder, filler, disintegrant, lubricant in tablets; preservative, antioxidant, corrigent, flavoring agent, cosolvent, emulsifier, solubilizer, osmotic pressure regulator, colorant, etc. in oral liquid preparation, and all of them can be called excipient.

The term "$C_{1-6}$ alkyl" as used in the present application refers to a straight or branched chain alkyl having 1 to 6 carbon atoms, such as $C_{1-4}$ alkyl, $C_{1-2}$ alkyl, $C_1$ alkyl, $C_2$ alkyl, $C_3$ straight or branched alkyl, $C_4$ straight or branched alkyl, $C_5$ straight or branched alkyl or $C_6$ straight or branched alkyl. Specific examples include, but are not limited to, methyl, ethyl, propyl, isopropyl, n-butyl, isobutyl, sec-butyl, tert-butyl, n-pentyl, and n-hexyl.

The term "$C_{1-6}$ alkoxy" as used in the present application refers to a $C_{1-6}$ alkyl as defined above which is attached to the parent molecular through an oxygen atom. Representative examples of $C_{1-6}$ alkoxy include, but are not limited to, methoxy, ethoxy, n-propoxy, isopropoxy, n-butoxy, isobutoxy, tert-butoxy, pentoxy, and hexyloxy.

The term "$C_{1-6}$ haloalkyl" as used in the present application refers to a $C_{1-6}$ alkyl as defined above which is mono- or poly-substituted with halogen such as fluorine, chlorine, bromine or iodine. Representative examples of $C_{1-6}$ haloalkyl include, but are not limited to, chloromethyl, chloroethyl, dichloroethyl, trifluoromethyl, difluoromethyl, and monofluoromethyl.

The term "$C_{1-6}$ alkyl-amino-" as used in the present application refers to an amino group monosubstituted with a $C_{1-6}$ alkyl as defined above. Typical examples of "$C_{1-6}$ alkyl-amino" include, but are not limited to, methylamino, ethylamino, propylamino, and butylamino.

The term "di($C_{1-6}$ alkyl)-amino-" as used in the present application refers to an amino group disubstituted with a $C_{1-6}$ alkyl as defined above. Typical examples of "di($C_{1-6}$ alkyl)-amino-" include, but are not limited to, dimethylamino, diethylamino, dipropylamino, and dibutylamino.

The term "$C_{3-6}$ cycloalkyl" as used in the present application refers to a saturated cyclic hydrocarbyl having 3 to 6 carbon atoms and having a monocyclic or bicyclic structure or multiple fused rings (including fused and bridged ring systems). Typical examples of "$C_{3-6}$ cycloalkyl" include, but are not limited to, cyclopropyl, cyclobutyl, cyclopentyl, and cyclohexyl.

The term "$C_{3-6}$ cycloalkoxy" as used in the present application refers to a $C_{3-6}$ cycloalkyl as defined above which is attached to the parent molecular through an oxygen atom. Typical examples of "$C_{3-6}$ cycloalkoxy" include, but are not limited to, cyclopropoxy, cyclobutoxy, cyclopentyloxy, and cyclohexyloxy.

The term "$C_{1-6}$ haloalkoxy" as used in the present application refers to a $C_{1-6}$ haloalkyl as defined above which is attached to the parent molecular through an oxygen atom. Representative examples of $C_{1-6}$ haloalkoxy include, but are not limited to, chloromethoxy, chloroethoxy, dichloroethoxy, trifluoromethoxy, difluoromethoxy, and monofluoromethoxy.

The term "subject" as used in the present application includes mammal.

The mammal described in the present application includes bovine, equine, caprinae, suidae, canine, feline, rodent, and primate, wherein the preferred mammal is human.

The term "effective amount" as used in the present application refers to an amount sufficient to achieve or at least partially achieve the desired effect. For example, a therapeutically effective amount refers to an amount sufficient to cure or at least partially suppress the disease and its complications in a patient already suffering from the disease. A prophylactically effective amount refers to an amount that can effectively prevent, suppress or delay the occurrence of a disease. Determination of such effective amount is well within the ability of those skilled in the art. For example, an amount effective for therapeutic use will depend on the severity of the disease to be treated, the general state of the patient's own immune system, the patient's general conditions such as age, weight, and sex, the route of administration of the drug, and other concurrently administered therapies and so on.

The amount of the compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof, which is administrated to a subject, depends on the type and severity of the disease or condition and the characteristics of the subject, such as general health, age, sex, weight, and tolerance to the drug, and also depends on the type of preparation and the route of administration of the drug, as well as factors such as the duration or interval of administration. Those skilled in the art will be able to determine appropriate dosages on the basis of these and other factors. In general, the compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof, has a daily dose for treatment that may be from about 0.0001 to 1000 mg/kg body weight/day, and the daily dose may be administered in one or more batches as appropriate.

The embodiments of the present application will be described in detail below with reference to the drawings and examples, but those skilled in the art will understand that the following drawings and examples are only used to illustrate the present application, rather than limit the scope of the present application. Various objects and advantages of the present application will become apparent to those skilled in the art according to the following detailed description of the drawings and preferred embodiments.

BRIEF DESCRIPTION OF THE DRAWINGS

FIG. 3 shows the inhibitory effect of Palovarotene on HBV infection in the infection model HepRG M14a.

SPECIFIC MODELS FOR CARRYING OUT THE INVENTION

Figure 1:
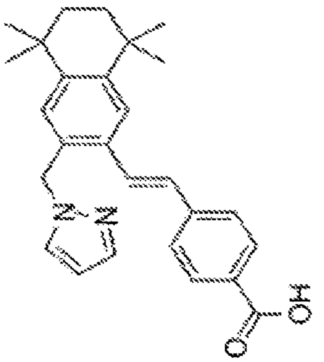
FIG. 1 shows the chemical structural formula of Palovarotene.

If no specific technique or condition is indicated in the following examples, the technique or condition described in the literature in the art or the product specification will be followed. Unless otherwise specified, the experimental methods are conventional methods, and the materials, reagents or equipment used without the manufacturer's indication are conventional products that can be commercially obtained. All experiments were repeated in three wells, and the results were the averaged values.

In the following examples, the drug to be tested was Palovarotene (purchased from MCE), and the positive control drugs included Entecavir (ETV, purchased from Yuanye Bio-Technology Co., Ltd.) and interferon IFNα (purchased from Sigma, SRP4595-100UG). During the experiments, the drug to be tested or the positive control drugs was diluted with medium to the desired final concentration, and the medium was determined according to the cells used, which were specifically described in each example.

In the following examples, the formula of 10 L of PBS used was: 80 g of NaCl, 2 g of KCl, 29 g of $Na_2HPO_4 \cdot 12H_2O$, 2.4 g of $KH_2PO_4$, which was mixed well with water and adjusted to have a pH of 7.4 and a metered volume of 10 L, then filtered with double layer 0.22 μm filtration membrane, subpackaged, and sterilized with high pressure steam for later use.

In the following examples, the DMEM medium used was purchased from SIGMA-ALDRICH, Art. No. D6429; FBS was purchased from ThermoFisher, Art. No. 10099141; Puromycin was purchased from InvivoGen, Art. No. ant-pr-1; Doxycycline was purchased from SIGMA-ALDRICH, Art. No. D9891; Penicillin and Streptomycin were purchased from Shandong Lukang Pharmaceutical Co., Ltd.; 4% PEG 8000 was purchased from AMRESCO, Art. No. 0159; WME medium was purchased from SIGMA-ALDRICH, Art. No. W1878; glutamine was purchased from SIGMA-ALDRICH, Art. No. G8540; insulin was purchased from Jiangsu Wanbang Biopharmaceuticals; hydrocortisone was purchased from Cayman, Art. No. 18226; Tetracycline was purchased from USB, Art. No. 22105-25g; B-27™ Supplement (50×) was purchased from GIBCO, Art. No. 17504044; Forskolin was purchased from MCE, Art. No. HY-15371; SB431542 was purchased from Tocris, Art. No. 1614; IWP2 was purchased from MCE, Art. No. HY-13912; DAPT was purchased from MCE, Art. No. HY-13027; LDN193189 was purchased from MCE, Art. No. HY-12071A.

In the following examples, the medium A used was DMEM medium, which contained: 10% FBS, 1 μg/mL Puromycin, 1 μg/mL Doxycycline, 100 U/mL penicillin and 100 μg/mL streptomycin.

In the following examples, the medium B used was DMEM medium, which contained: 10% FBS, 1 μg/mL Puromycin, 100 U/mL penicillin and 100 μg/mL streptomycin.

In the following examples, the medium C used was DMEM medium (freshly prepared just before use), which contained 4 w/v % PEG 8000, 1 μg/mL Puromycin, 1 μg/mL Doxycycline, 100 U/mL penicillin, 100 μg/mL streptomycin and 5% FBS.

In the following examples, the medium D used was WME medium, which contained: 10% FBS, 100 mM glutamine, 5 μg/mL insulin, 50 μM hydrocortisone, 100 U/mL penicillin and 100 μg/mL streptomycin.

In the following examples, the medium E used was WME medium (freshly prepared just before use), which contained 4 w/v % PEG 8000, 100 mM glutamine, 5 μg/mL insulin, 50 μM hydrocortisone, 100 U/mL penicillin, 100 μg/mL streptomycin, and 5% FBS.

In the following examples, the medium F used was DMEM medium, which contained: 10% FBS, 100 U/mL penicillin and 100 μg/mL streptomycin.

In the following examples, the medium G used was DMEM medium, which contained: 10% FBS, 1 μg/mL Tetracycline, 100 U/mL penicillin and 100 μg/mL streptomycin.

In the following examples, the medium H used was WME medium, which contained: 1 v/v % B-27™ Supplement (diluted at a ratio of 1:100 when used, that was, every 100 mL of medium H contained 1 mL of B-27™ Supplement), 20 μmol/L Forskolin, 10 μmol/L SB431542, 0.5 μmol/L IWP2, 5 μmol/L DAPT, 0.1 μmol/L LDN193189, 100 U/mL penicillin and 100 μg/mL streptomycin.

In the following examples, the medium I used was WME medium (freshly prepared just before use), which contained 4 w/v % PEG 8000, 20 μmol/L Forskolin, 10 μmol/L SB431542, 0.5 μmol/L IWP2, 5 μmol/L DAPT, 0.1 μmol/L LDN193189, 100 U/mL Penicillin, 100 μg/mL Streptomycin and 0.5 v/v % B-27™ Supplement (diluted at a ratio of 1:200 when used, that was, every 100 mL of medium I contained 0.5 mL of B27™ Supplement).

Example 1: Evaluation of the Inhibitory Effect of Test Drug on Hbv Infection in Infection Model Hepg2-Hntcp 2B1

The human sodium-taurocholate cotransporting polypeptide (hNTCP) gene and the red fluorescent protein (mCherry) gene were constructed in a bicistronic expression cassette regulated by tetracycline-inducible promoter, the expression cassette was stably integrated into HepG2-Tet On cells by using a lentiviral system, a stable cell line HepG2-hNTCP 2B1 with high expression of hNTCP was obtained by using flow cytometry sorting technology, and this cell model supported HBV infection and generated HBV-related indicators. (For the construction method of this cell model, please refer to: Ya-Li Zhang, Ying Gao, Jia-Li Cao, Jing-Hua Zhao, Tian-Ying Zhang, ChuanLai Yang, Hua-Long Xiong, Ying-Bin Wang, Shan-Hai Ou, Tong Cheng, Chang-Rong Chen, Quan Yuan & Ning-Shao Xia (2019), Robust in vitro assay for analyzing the neutralization activity of serum specimens against hepatitis B virus, Emerging Microbes & Infections, 8:1, 724-733, DOI: 10.1080/22221751.2019.1619485).

This experiment was carried out in a 24-well culture plate. Each drug to be tested in the experimental group had three final concentrations of 1 μM, 5 μM and 25 μM, and Entecavir (ETV) in the positive control group had a final concentration of 1 μM, in which the drug to be tested and the positive control drug were diluted with medium A to the desired concentrations, and to the blank group the same volume of medium A without drug was added.

About $1.5 \times 10^5$ HepG2-hNTCP 2B1 cells were plated in each well, and 500 μL of medium B was added. After the cells adhered, medium A was used for replacement to perform the induction with Doxycycline during the whole experiment.

After 72 hours of the induction with Doxycycline, 500 μL of drug-containing medium A was added to each well to perform drug treatment for 24 h, and then the cells were infected with HBV, the virus amount for infection per well was 100 MOI. Before infection, HBV solution was obtained by diluting HBV in medium C, and the infection volume was 250 μL per well. During infection, the cell supernatant was first removed by suction, the HBV solution was added to the cells, then the cells were incubated for 16-20 hours, and then the supernatant was collected as the sample of Day 0. Then the cells were washed three times with PBS warmed in 37° C. bath, and fresh drug-containing medium A (500 μL) was used for replacement, then the supernatant was collected every 2 days for detection, fresh drug-containing medium A was added, on the 8th day, all the supernatant and cells were collected for related detection. The detection items included: HBsAg/HBeAg, HBV DNA, HBV cccDNA.

HBsAg/HBeAg Detection:

HBsAg (chemiluminescence enzyme immunoassay (CLEIA), product standard number: YZB/Guo 0346-2014) and HBeAg (enzyme-linked immunosorbent assay (ELISA), product standard number: YZB/Guo 0216-2013) were detected using the Beijing Wantai Company's detection kits, and the specifical detection operations were carried out according to the detection methods described in the instructions in the kits.

HBV DNA Detection:

After the collected cells were washed with PBS, automated extraction was performed on a nucleic acid extraction workstation (purchased from GenMagBio, model: DOF-9696) using a viral DNA & RNA extraction kit (Beijing GenMagBio) (for the extraction procedure, please refer to the instrument manual) to obtain HBV DNA. The HBV DNA was quantified by probe real-time fluorescent quantitative PCR, in which the reagent used was Premix Ex Taq™ (Takara), the instrument used was Roche's LightCycler® 96, the primer sequences used for fluorescence quantification were shown in Table 1, and the fluorescence quantitative reaction system was shown in Table 2.

HBV cccDNA Detection:

The modified Hirt method was used to extract HBV cccDNA by using a kit, and the kit used was a plasmid mini kit (TIANGEN BIOTECH (BEIJING) CO.,LTD.), in which the solutions involved were Buffer I (50 mM Tris, 10 mM EDTA, pH 7.5), Buffer II (1.2% SDS), Buffer III (3M CsCl, 1M potassium acetate, 0.67M acetic acid), and for the specific method, please refer to the plasmid extraction method described in the kit instructions. The HBV cccDNA was quantitatively detected by probe real-time fluorescence quantitative PCR, and mitochondrial DNA (mtDNA) was simultaneously detected as an internal reference, in which the instrument used was Roche's LightCycler® 96, the primers used for fluorescence quantification were shown in Table 1, and the fluorescence quantitative reaction system was shown in Table 2.

The fluorescence reaction procedure for quantitative detection was as follows:

(1) HBV DNA quantification: the quantification program was 95° C., 30 s; (95° C., 5 s; 60° C., 30 s) for 45 cycles, and the fluorescence channel was Hex.

(2) cccDNA quantification: the quantitative program was 95° C., 5 min; (95° C., 30 s; 60° C., 60 s) for 45 cycles, and the fluorescence channel was FAM.

(3) mtDNA quantification: the quantitative program was 95° C., 5 min; (95° C., 30 s; 55° C., 40 s) for 45 cycles, and the fluorescence channel was Hex.

Calculation of cccDNA normalization: the specific formula was as follows: 2^(mtDNA-cccDNA), in which those in the bracket were Ct values of mtDNA and cccDNA respectively.

Figure 2:
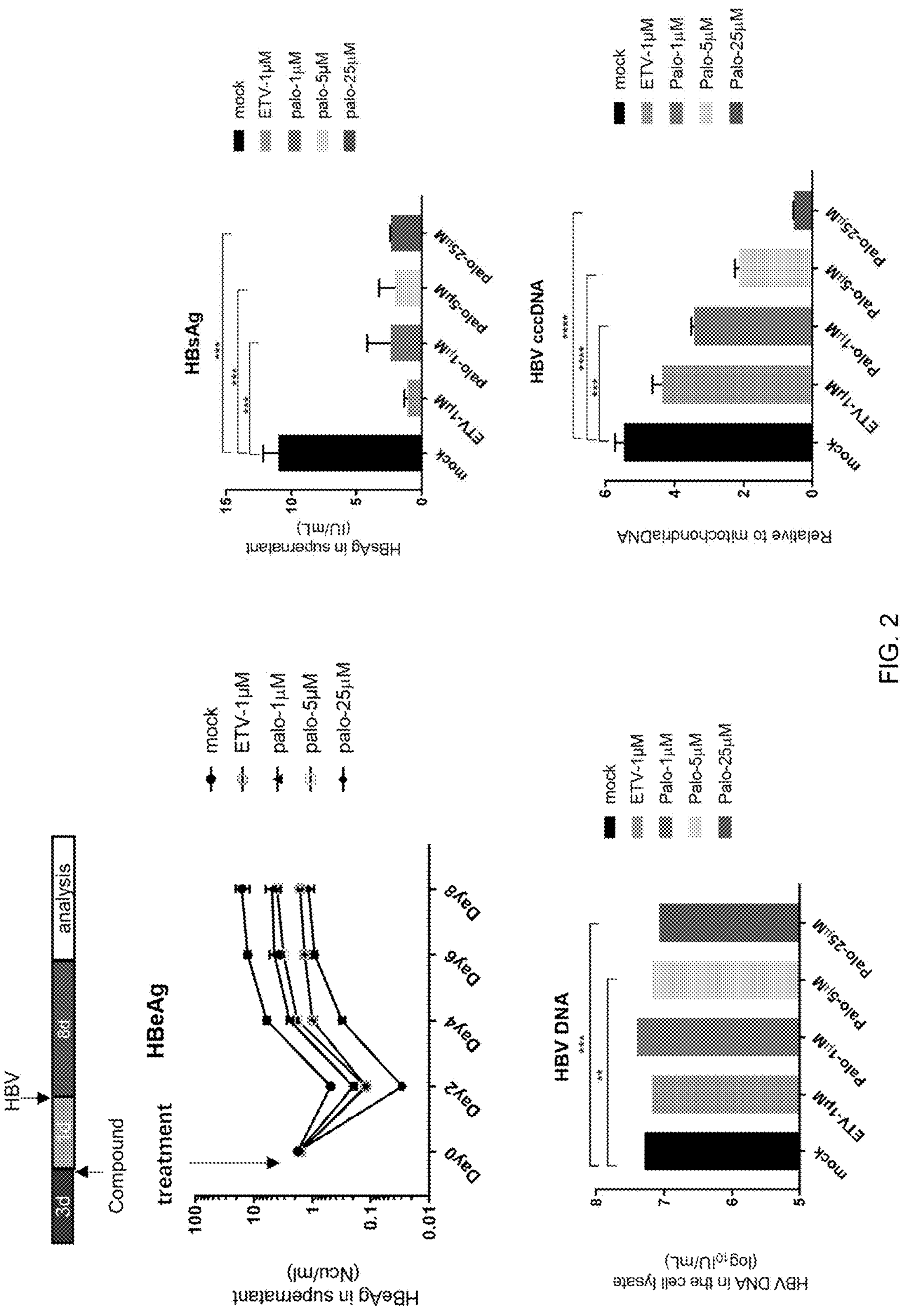
FIG. 2 shows the inhibitory effect of Palovarotene on HBV infection in the infection model HepG2-hNTCP 2B1.

The experimental results were shown in FIG. 2. The results showed that compared with the blank group, Palovarotene treatment could effectively inhibit the levels of HBsAg ($p<0.05$) and HBeAg ($p<0.05$) in the cell supernatant, the levels of intracellular HBV DNA ($p<0.001$) and HBV cccDNA ($p<0.0001$), and the degree of inhibition was dose-dependent in some extent.

This indicated that Palovarotene could significantly inhibit HBV from infecting HepG2-hNTCP 2B1.

TABLE 1

PCR primer sequences

| Application | Name | Sequence (5'-3') |
|---|---|---|
| HBV DNA detection | HBV-F | TTTCACCTCTGCCTAATCAT |
| HBV DNA detection | HBV-R | TCAGAAGGCAAAAAAGAGAG TAACTC |
| HBV DNA detection | HBV-Probe | HEX-CCTTGGGTGGCTTTGG GGCATGGA-BHQ1 |
| HBV cccDNA detection | cccDNA-Probe | FAM-ACCGTGAACGCCCACC GAATGTTGC-BHQ1 |
| HBV cccDNA detection | cccDNA-F | TGCACTTCGCTTCACCT |
| HBV cccDNA detection | cccDNA-R | AGGGGCATTTGGTGGTC |
| mtDNA detection | mt4987F | CCCAGCTACGCAAAAT |
| mtDNA detection | mt5106R | AATGCGGTAGTAGTTAGGA TA |
| mtDNA detection | mt5010-Probe | HEX-CATACTCCTCAATTA CCCACATAG-BHQ1 |

TABLE 2 qPCR quantitative reaction system

| Components | 20 μL Reaction |
|---|---|
| 2* Premix Ex Taq (Probe qPCR) | 10 μL |
| Forward Primer (100 μM) | 0.1 μL |
| Reverse Primer (100 μM) | 0.1 μL |
| Probe (100 μM) | 0.05 μL |
| DEPC | 4.75 μL |
| Template | 5 μL |

Example 2: Evaluation of the Inhibitory Effect of Drug to be Tested on Hbv Infection in Infection Model Heparg M14A HepaRG was a hepatic progenitor cell line with differentiation potential which was isolated from the tumor tissue of a female hepatitis C patient. After two weeks of cell plating, the cellular differentiation was induced with 2% DMSO (2 mL of DMSO was added to per 100 mL of cell culture medium) for two weeks. Finally, about 50% of the cells differentiated into hepatocyte-like cells, and the other 50% of the cells differentiated into cholangiocyte-like cells. Among them, hepatocyte-like cells supported HBV infection with an infection efficiency of about 20%. Through genetic modification of HepaRG, the HNF4A and FoxM1 genes were integrated into HepaRG cells, and a HepaRG M14A cell line that could complete differentiation and support HBV infection independent of DMSO was obtained by screening. (For the construction method of this cell model, please refer to: Zhao Jinghua. Development, Optimization and Preliminary Application of in vitro models supporting HBV Infection [D]. Xiamen University, 2016.)

This experiment was carried out in a 24-well cell culture plate. Each drug to be tested in the experimental group had three final concentrations of 1 μM, 5 μM and 25 μM, and Entecavir (ETV) in the positive control group had a final concentration of 1 μM, in which the drug to be tested and the positive control drug were diluted with medium D to the desired concentrations, and to the blank group the same volume of medium D without drug was added. About $1.5\times10^5$ HepaRG M14A cells were plated in each well, and 500 μL of medium D was added to each well. After cell plating, medium D was replaced every 2 days. After 13 days of cell plating, medium D was replaced with drug-containing medium D for drug treatment. After 24 hours of drug treatment, the cells were infected with HBV, and the amount of HBV for infection in each well was 1000 MOI. Before infection, an HBV solution was obtained by diluting HBV in medium E, and the infection volume was 250 μL per well. During infection, the cell supernatant was first removed by suction, the HBV solution was added to the cells, then the cells were incubated for 24 hours, and then the supernatant was collected as the sample of Day 0. Then, the cells were washed three times with PBS warmed in bath at 37° C., and fresh drug-containing medium D (500 μL per well) was used for replacement, then the supernatant was collected every 2 days for detection, and fresh drug-containing medium D was used for replacement, until the 8th day, all the supernatant and cells were collected for related detection. The detection items include HBsAg, HBeAg, HBV DNA, HBV cccDNA, and for the detection method, please refer to Example 1.

Figure 3:
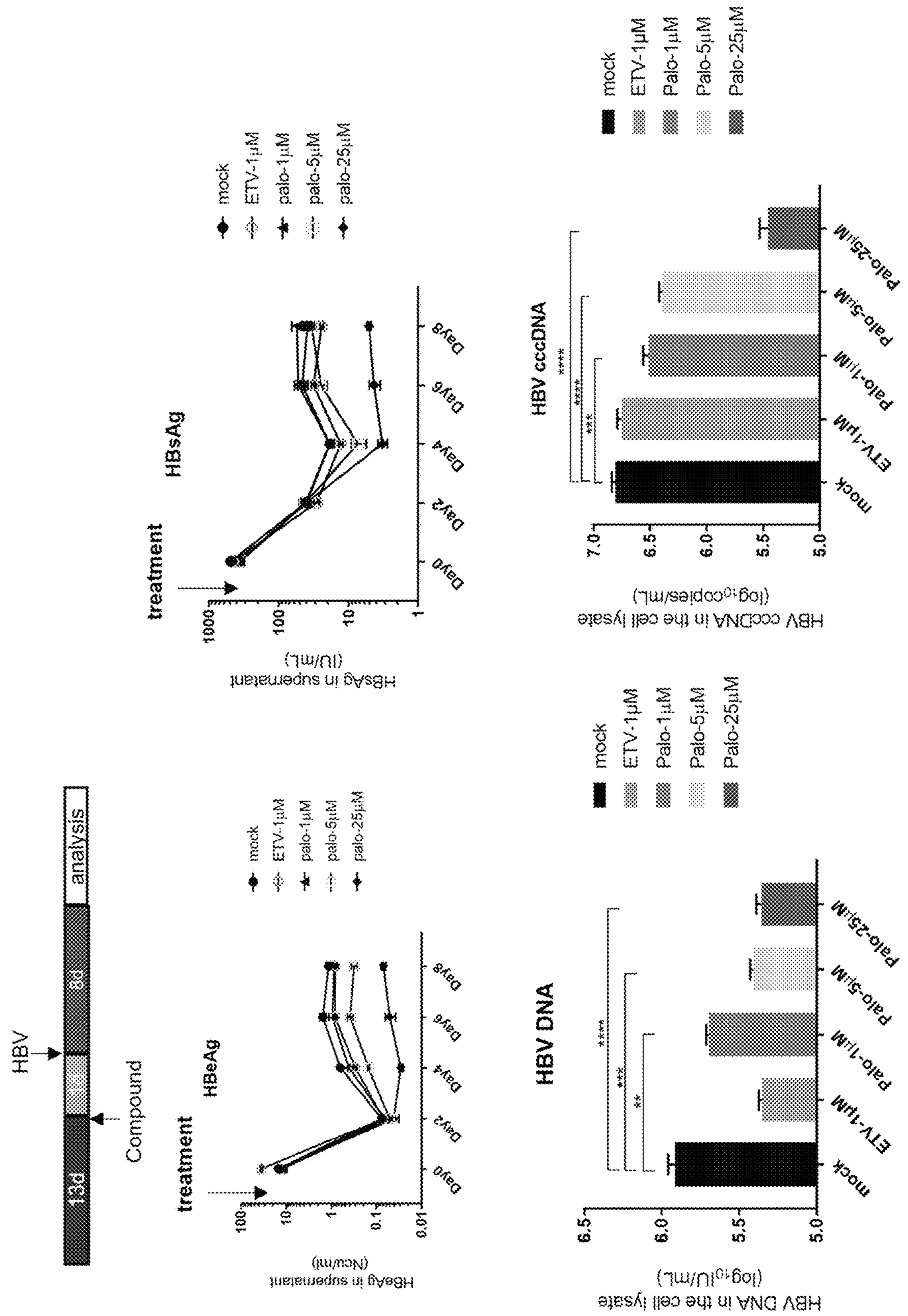

The experimental results were shown in FIG. 3. The results showed that in the HepaRG M14a infection cell model, the Palovarotene treatment before infection could significantly reduce the levels of HBsAg ($p<0.05$) and HBeAg ($p<0.05$) in cell supernatant, and the levels of intracellular HBV DNA ($p<0.0001$) and cccDNA ($p<0.0001$).

The above results indicated that Palovarotene could significantly inhibit HBV from infecting HepaRG M14A.

Example 3. Evaluation of Therapeutic Effect of Drug to be Tested on the Infection Model Hepg2-Hntcp 2B1 Infected by Hbv This experiment was carried out in a 24-well culture plate. Each drug to be tested in the experimental group had three final concentrations of 1 μM, 5 μM and 25 μM, and ETV in the positive control group had a final concentration of 1 μM, in which the drug to be tested and the positive control drug were diluted with medium A to the desired concentrations, and to the blank group the same volume of medium A without drug was added. About $1.5\times10^5$ HepG2-hNTCP 2B1 cells were plated in each well, and 500 μL of medium B was added to each well. After the cells adhered, medium A was used for replacement to perform the induction with Doxycycline during the whole experiment.

4 Days after the induction with Doxycycline, HBV infection was performed, and the amount of HBV in each well was 100 MOI. Before infection, HBV was diluted in medium C to obtain HBV solution, and the infection volume was 250 μL per well. During infection, the cell supernatant was first removed by suction, the HBV solution was added to the cells, and the cells were incubated for 24 hours, then the supernatant was collected as the sample of Day 0. Then the cells were washed three times with PBS, and fresh medium C was used for replacement. After that, the supernatant was collected every two days for detection, fresh medium C was used for replacement. On the 6th day, fresh drug-containing medium A was used for replacement to start drug treatment, then the supernatant was collected every two days for detection, and fresh drug-containing medium A was used for replacement, until the 12th day, all the supernatant and cells were collected for relevant detection. The detection items included HBsAg, HBeAg, HBV DNA, HBV cccDNA, and for the detection method, please refer to Example 1.

Southern blot experiment was carried out on a 10 $cm^2$ culture plate. About $5\times10^6$ HepG2-hNTCP 2B1 cells were plated in each 10 $cm^2$ culture plate, and medium B was added. After the cells adhered, medium A was used for replacement to perform the induction with Doxycycline during the whole experiment. HBV infection was performed 4 days after the induction with Doxycycline, and the amount of HBV for infection was 1000 MOI. Before infection, HBV was diluted in medium C to obtain HBV solution, and the infection volume was 5 mL. During infection, the cell supernatant was first removed by suction, the HBV solution was added to the cells, the cells were incubated for 24 hours, then the supernatant was collected as the sample of Day 0. Then the cells were washed three times with PBS, and fresh medium A was used for replacement. After that, the supernatant was collected every two days for detection, fresh medium A was used for replacement. On the 6th day, fresh drug-containing medium was used for replacement to start drug treatment (the drug concentration for treatment was 5 μM, the control group used interferon IFNα at a concentration of 500 IU for treatment), and then supernatant was collected every two days for detection, and fresh drug-containing medium A was used for replacement, until the 12th day, all the supernatant and cells were collected for Southern blot detection and immunofluorescence detection.

Southern Blot Detection

The modified Hirt method was used to extract HBV cccDNA by using a kit, and the kit used was Qiagen plasmid midi kit. For the specific extraction operation, please refer to the plasmid extraction method of the kit. The specific steps of Southern blot detection were as follows:

a. A loading buffer (purchased from TaKaRa Company) was added to the extracted HBV cccDNA sample, and then the DNA was separated by electrophoresis through 1.2% agarose gel at 80V in 1×TAE buffer (40 mmol/L Tris Base, 1 mmol/L EDTA, 20 mmol/L sodium acetate) for 2 hours; then the gel was placed in a depurination buffer (0.2 mol/L HCl), and soaked for 15 min at room temperature with shaking, and then rinsed twice with sterilized ultrapure water, 1 min each time; then the gel was placed in a denaturation buffer (0.5 mol/L NaOH, 1.5 mol/L NaCl), and soaked for 30 min at room temperature with shaking, then rinse twice with sterilized ultrapure water, 1 min each time; and finally soaked in a neutralization buffer (1 mol/L Tris-base, 1.5 mol/L NaCl) for 10 min.

b. Transfer from gel to membrane: The gel was soaked in 10×SSC (1.5 mol/L NaCl, 0.15 mol/L trisodium citrate, pH 7.0) for 5 min, during which the filter paper and nylon membrane (purchased from Roche) were first wetted with sterilized ultrapure water and then soaked in 10×SSC; the nucleic acid was transferred to the nylon membrane using a vacuum blotting apparatus (the pressure was adjusted to 5 MPa, the transfer time was 90 min), and a hybridization solution (DIG Easy Hyb™ Granules, purchased from Roche, Art. No. 38716500) was preheated at 42° C. at the same time. After the transfer, the blotted nylon membrane was cross-linked for 3 min under the irradiation dose of 1.5 J/$cm^2$ using an UV cross-linking instrument SiGmA SH4 B type (purchased from Shanghai Sigma Co., Ltd.).

c. Hybridization: The membrane was soaked in the pre-warmed hybridization solution at 42° C., and was placed in a hybridization oven to be incubated at 42° C. for 2 h. At the same time, the probe was heated at 95° C. for 10 min and then quickly inserted into the ice-water mixture for 5 min (to prevent renaturation), then diluted in the hybridization solution (300 ng of probe was added to per 10 mL of hybridization solution), and hybridized with the membrane at 42° C. for 12 h. After the hybridization was completed, the membrane was washed three times at room temperature with Wash buffer I (2×SSC, 0.1% SDS), 5 min each time, and then washed three times with Wash buffer II (0.5×SSC, 0.1% SDS) at 65° C., 15 minutes each time.

d. Antibody incubation: First, the membrane was soaked in a maleic acid buffer (0.1 mol/L maleic acid, 0.15 mol/L NaCl, pH 7.5) for 2 min, and then blocked with 1× Blocking buffer (purchased from SIGMA-ALDRICH, Art. No. B6429-500ML) (diluted with maleic acid buffer) at room temperature for 1 h. After blocking, anti-Dig-AP antibody (purchased from SIGMA-ALDRICH, Art. No. Roche-11093274910) was diluted with 1× Blocking buffer, and the membrane and the antibody were incubated at room temperature for 40 min. After incubation, the membrane was washed three times with a rinsing solution (0.1 mol/L maleic acid, 0.15 mol/L NaCl, 0.3 vol. % Tween 20, pH 7.5) at room temperature, 15 min each time.

e. Detection: First, the membrane was soaked in an equilibrium solution (0.1 mol/L Tris-base, 0.1 mol/L NaCl, pH 9.5) for 3 minutes, then the membrane was taken out and a chromogenic substrate (CDP-star, purchased from Roche) was added to the membrane, and finally exposed on a biomolecular imager (ImageQuant LAS 4000 mini, GE).

Immunofluorescence Detection

The HBcAg immunofluorescence staining involved in this experiment was performed directly on adherent cells. The following operations were performed on a shaker at 100 rpm/min. The cells in the cell culture plate were washed once with PBS. Fixation: 4% paraformaldehyde (purchased from Beyotime, Art. No. P0099-100 ml) was added to cover the cells, then the cells were incubated at room temperature for 10 min in the dark. Washing: the cells were washed three times with PBS, 3 min each time. Permeabilization: 0.2% Triton X-100 (purchased from AIVIRESCO) was added, and the cells were incubated at room temperature for 10 min. Washing: the cells were washed three times with PBS, 3 min each time. Blocking: 3% BSA (3 g of BSA powder was weighed, and dissolved in 100 mL of PBS, in which BSA powder was purchased from SIGMA-ALDRICH) was added, and the cells were incubated at room temperature for 60 min or at 4° C. overnight. Primary antibody: Anti-HBcAg (2A7, mouse antibody) was diluted at a ratio of 1:1000 with 3% BSA, then was added to the wells with 200 μL per well, and then the cells were incubated at room temperature for 1 hour or at 4° C. overnight. Washing: the cells were washed three times with PBS, 3 min each time. Secondary antibody: secondary antibody (Alexa Fluor® 488 Donkey Anti-Rabbit IgG (H+L) (Invitrogen)) was diluted at a ratio of 1:1000 with 3% BSA, then was added to the wells with 200 μL per well, and then the cells were incubated at room temperature for 30 min. Washing: the cells were washed three times with PBS, 3 min each time. Nuclei staining: DAPI (Invitrogen) was diluted at a ratio of 1:2000 with 3% BSA, then was added to the wells with 200 μL per well, and then the cells were incubated at room temperature for 5 min. Washing: the cells were washed three times with PBS, 3 min each time. Photographing: Photographing was performed with a high-content confocal microscope (PerkinElmer, Operetta CLS), and the mean fluorescence intensity of green fluorescence was analyzed.

Figure 4:
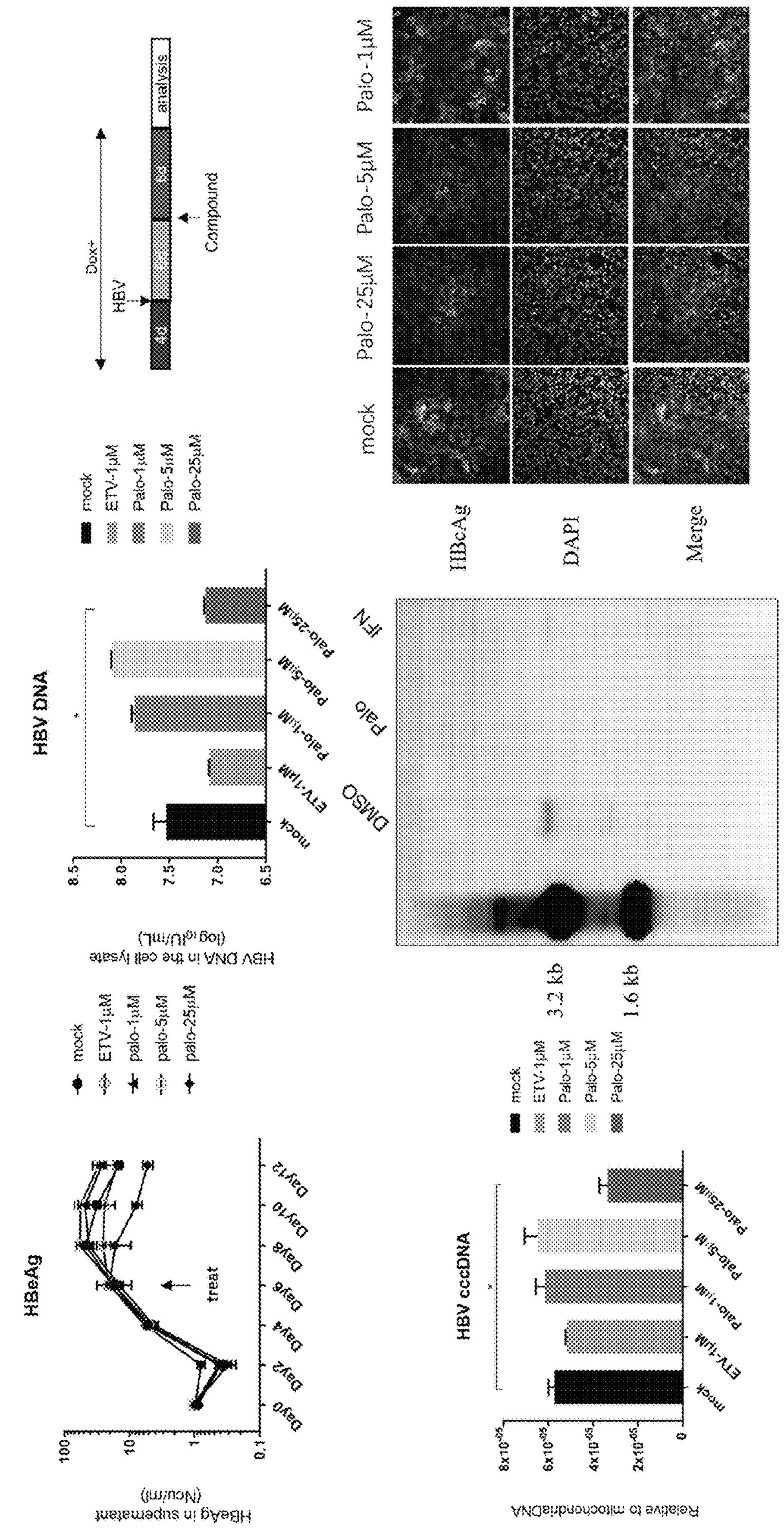
FIG. 4 shows the therapeutic effect of Palovarotene on the infection model HepG2-hNTCP 2B1 infected by HBV.

The experimental results were shown in FIG. 4. The results showed that after the drug treatment that was performed 6 days after HBV infection, Palovarotene at high concentrations had a significant inhibitory effect on HBeAg ($p<0.05$), and could significantly reduce the levels of HBV DNA ($p<0.05$) and HBV cccDNA ($p<0.05$), while the control group (ETV) and the blank group showed no significant difference. The results of Southern blot showed that the level of HBV cccDNA after the drug treatment at concentration of 5 μM was significantly lower than that of the interferon treatment in the control group and the blank group without drug. Immunofluorescence results showed that Palovarotene could significantly reduce the positive rate of HBcAg in HepG2-hNTCP 2B1 cells after infection, suggesting that the drug treatment could inhibit HBV infection.

High-concentration Palovarotene treatment could significantly inhibit HBV viral replication and e-antigen levels after infection.

Example 4. Evaluation of Therapeutic Effect of Drug to be Tested on Hepad38 that can Produce High Levels of Hbv DNA HepAD38 is a hepatoma cell line (D genotype) that stably integrates the HBV genome, it expresses HBV under conditions that may be regulated with tetracycline. In the presence of tetracycline, the cell line does not synthesize virus particles due to the repression of HBV pgRNA synthesis; in the absence of tetracycline, the HepAD38 cell line transcribes HBV pgRNA, synthesizes subviral particles and secretes virion-like particles into the cell supernatant. The HepAD38 has a DNA level about 10 times that of HepG2.2.15, and thus is a high-copy HBV in vitro replication cell model (for the construction method of this cell model, please refer to: Ladner S K, Otto M J, Barker C S, et al. Inducible expression of human hepatitis B virus (HBV) in stably transfected hepatoblastoma cells: a novel system for screening potential inhibitors of HBV replication. Antimicrob Agents Chemother. 1997; 41(8):1715-1720.).

This experiment was carried out in a 24-well culture plate. Each drug to be tested in the experimental group had two final concentrations of 1 μM and 5 μM, and ETV in the positive control group had a final concentration of 1 μM, in which the drug to be tested and the positive control drug were diluted with medium F to the desired concentrations, and to the blank group the same volume of medium F without drug was added. About $4\times10^5$HepAD38 cells were plated in each well, 500 μL of medium G containing tetracycline hydrochloride (Tetracycline) was added to each well, Day 0 was set 48 h after the cells were plated, and the medium G containing tetracycline hydrochloride (Tetracycline) was removed at the same time, fresh drug-containing medium F was used for replacement, and then fresh drug-containing medium F was used for replacement every two days until the 8th day, and the levels of HBsAg in the cell supernatant and intracellular HBV DNA were detected on the 8th day. For the method for detection, please refer to Example 1.

The Southern blot experiment was performed on 6 $cm^2$ culture plates. About $4.2\times10^6$ HepAD38 cells were plated in each 6 $cm^2$ culture plate, and medium G containing tetracycline hydrochloride (Tetracycline) was added. During the experiment, the medium G containing tetracycline hydrochloride was removed, and the drug-containing medium F was added at the same time for drug treatment, in which the treatment concentration of test drug Palovarotene was 5 μM, and the control group used Entecavir (ETV) at a concentration of 5 μM for treatment, and the treatment time was 8 days.

The specific Southern blot detection method was carried out with reference to Example 3.

Figure 5:
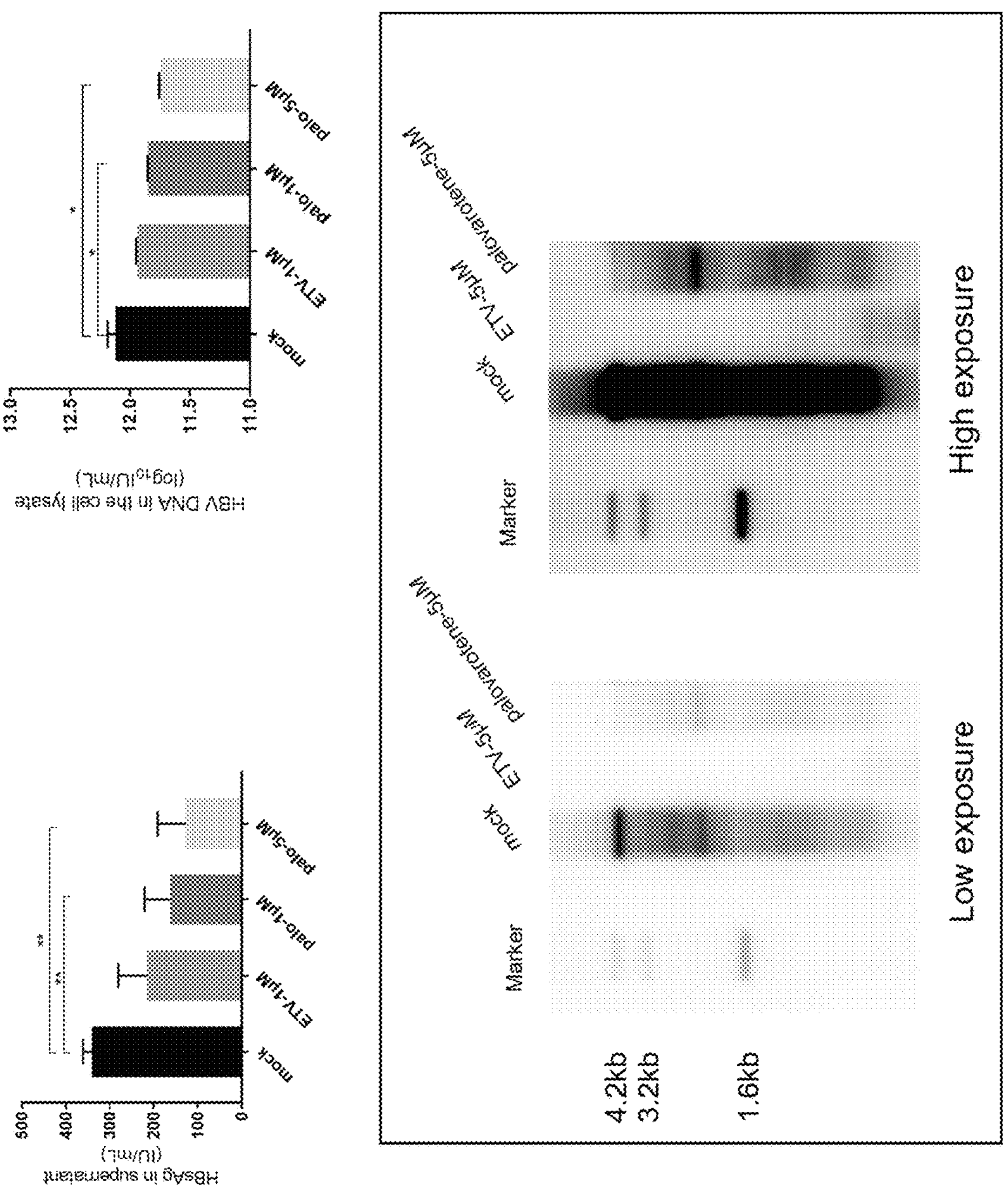
FIG. 5 shows the evaluation results of Palovarotene in the high copy replication model HepAD38.

The results were shown in FIG. 5. The results showed that Palovarotene at concentration of 5 μM had a significant inhibitory effect on the surface antigen production ($p<0.01$) and HBV DNA ($p<0.05$) of the replication model HepAD38. The Southern blot results showed that the drug could significantly inhibit the level of HBV cccDNA, but the inhibitory effect was inferior to that of the control group (ETV).

The Palovarotene treatment could significantly inhibit the virus replication level in the replication model HepAD38.

Example 5: Evaluation of Inhibitory Effect of Drug to be Tested on Hbv Infection in Human Primary Hepatocytes In this experiment, experimental group, positive control group and blank group were set, in which each drug to be tested (Palovarotene) in the experimental group had three final concentrations of 1 μM, 5 μM and 25 μM, and ETV in the positive control group had a final concentration of 1 μM, in which the drug to be tested and the positive control drug were diluted in medium H to the desired concentrations, and to the blank group the same volume of medium H without drug was added.

Primary hepatocytes were isolated from humanized mice transplanted with primary human hepatocytes through perfusion technique (refer to: Foquet, Lander, et al. "Successful engraftment of human hepatocytes in uPA-SCID and FRG® KO mice." Hepatocyte Transplantation. Humana Press, New York, NY, 2017. 117-130, Wan-Chun Li, et al. "Isolation and Culture of Adult Mouse Hepatocytes." Mouse Cell Culture. Humana Press, 2010. 185-196.), directly cultured in 24-well plates (Collagen I pre-coated 24-well plates, purchased from Thermo Scientific) after counting (about $5\times10^5$ primary hepatocytes per well), and medium H was added to maintain hepatocyte morphology (refer to: Xiang, Chengang, et al. "Long-term functional maintenance of primary human hepatocytes in vitro." Science 364.6438 (2019): 399-402.). After culturing for 24 hours, drug-containing medium H was used to replace the drug-free medium H to perform drug treatment for 24 hours, and then infection was carried out with HBV, and the amount of HBV for infection in each well was 2000 MOI. Before infection, HBV was first diluted in medium I to obtain HBV solution, and the infection volume was 250 μL/well. During infection, the cell supernatant was first removed by suction, the HBV solution was added to the cells, the cells were incubated for 24 hours, then the supernatant was collected as the sample of Day 0. Then the cells were washed 3 times with PBS that was warmed in bath at 37° C., and fresh drug-containing medium H (500 μL per well) was used for replacement, then the supernatant was collected every two days for detection, fresh drug-containing medium H was used for replacement, until the 8th day, all the supernatants and cells were collected for relevant detection. The detection items included HBsAg, HBeAg, HBV DNA, HBV cccDNA, and for the detection method, please refer to Example 1.

Figure 6:
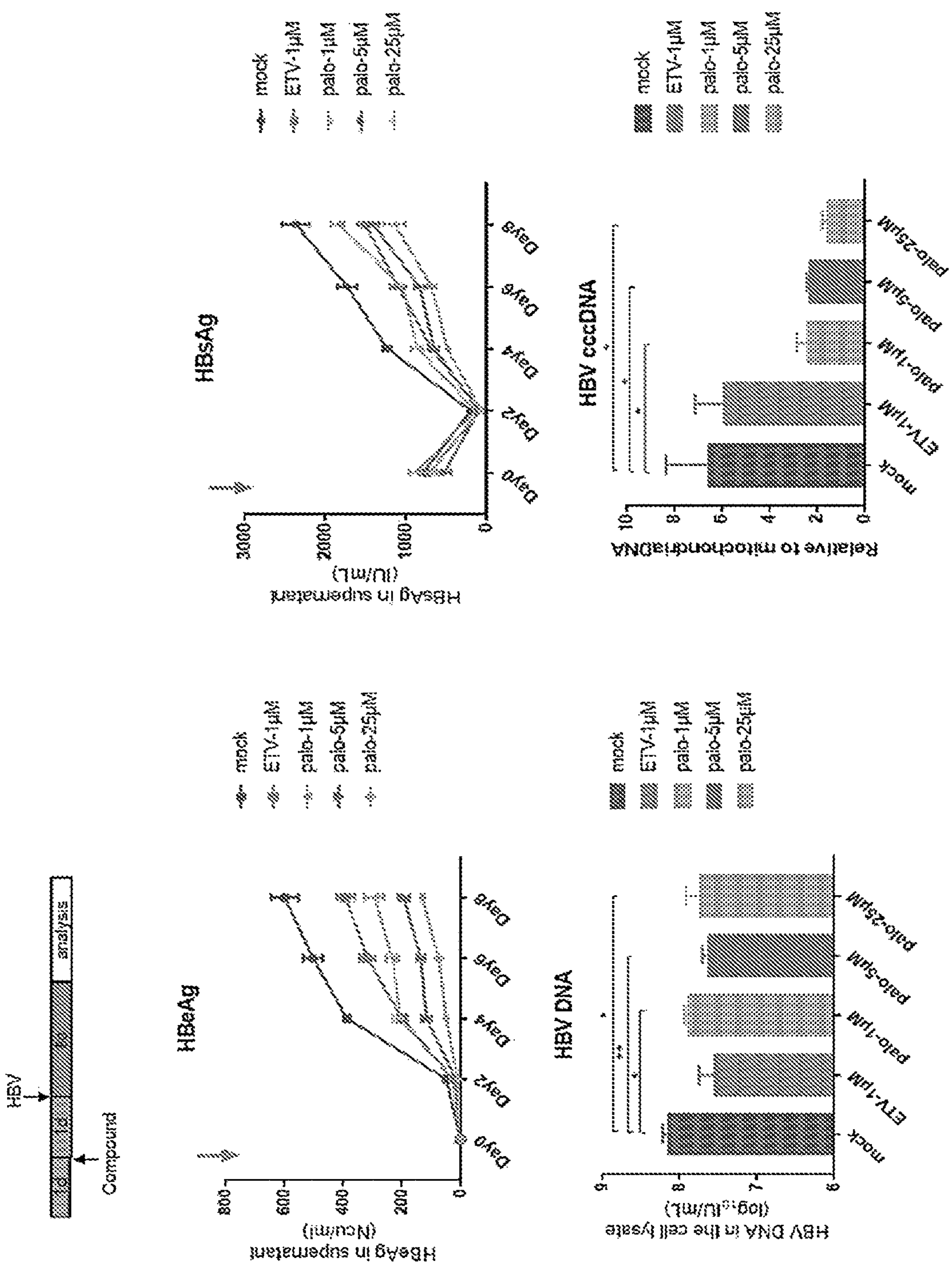
FIG. 6 shows the inhibitory effect of Palovarotene on HBV infection in human primary hepatocytes.

The experimental results were shown in FIG. 6. The results showed that in human primary hepatocytes, Palovarotene treatment before infection could significantly inhibit the levels of HBsAg ($p<0.05$) and HBeAg ($p<0.05$) in the cell supernatant, and the levels of intracellular HBV DNA ($p<0.05$) and cccDNA ($p<0.05$).

The Palovarotene treatment could significantly inhibit HBV from infecting primary human hepatocytes.

Example 6: Evaluation of Therapeutic Effect of Drug to be Tested on Human Primary Hepatocytes Infected by Hbv In this experiment, experimental group, positive control group and blank group were set, in which each drug to be tested (Palovarotene) in the experimental group had three final concentrations of 1 μM, 5 μM and 25 μM, and ETV in the positive control group had a final concentration of 1 μM. The drug to be tested and the positive control drug were diluted with medium H to the required concentrations, and to the blank group the same volume of medium H without drug was added.

Primary hepatocytes were isolated from humanized mice transplanted with primary human hepatocytes through perfusion technique, directly cultured in 24-well plates after counting ($5\times10^5$ primary hepatocytes per well), and medium H was added to maintain hepatocyte morphology. Infection with HBV was performed 24 hours after culturing, the amount of HBV for infection in each well was 2000 MOI. Before infection, HBV was first dissolved in medium I to obtain HBV solution, and the infection volume was 250 μL/well. During infection, the cell supernatant was first removed by suction, the HBV solution was added to the cells, the cells were incubated for 24 hours, then the supernatant was collected as the sample of Day 0, and then the supernatant was collected every two days for detection, fresh medium H was used for replacement. On the 8th day, fresh drug-containing medium H was used for replacement to start the drug treatment, until the 14th day, all the supernatant and the cells were collected for relevant detection. The detection items included: HBsAg, HBeAg, HBV DNA, HBV cccDNA, and for the detection method, please refer to Example 1.

Figure 7:
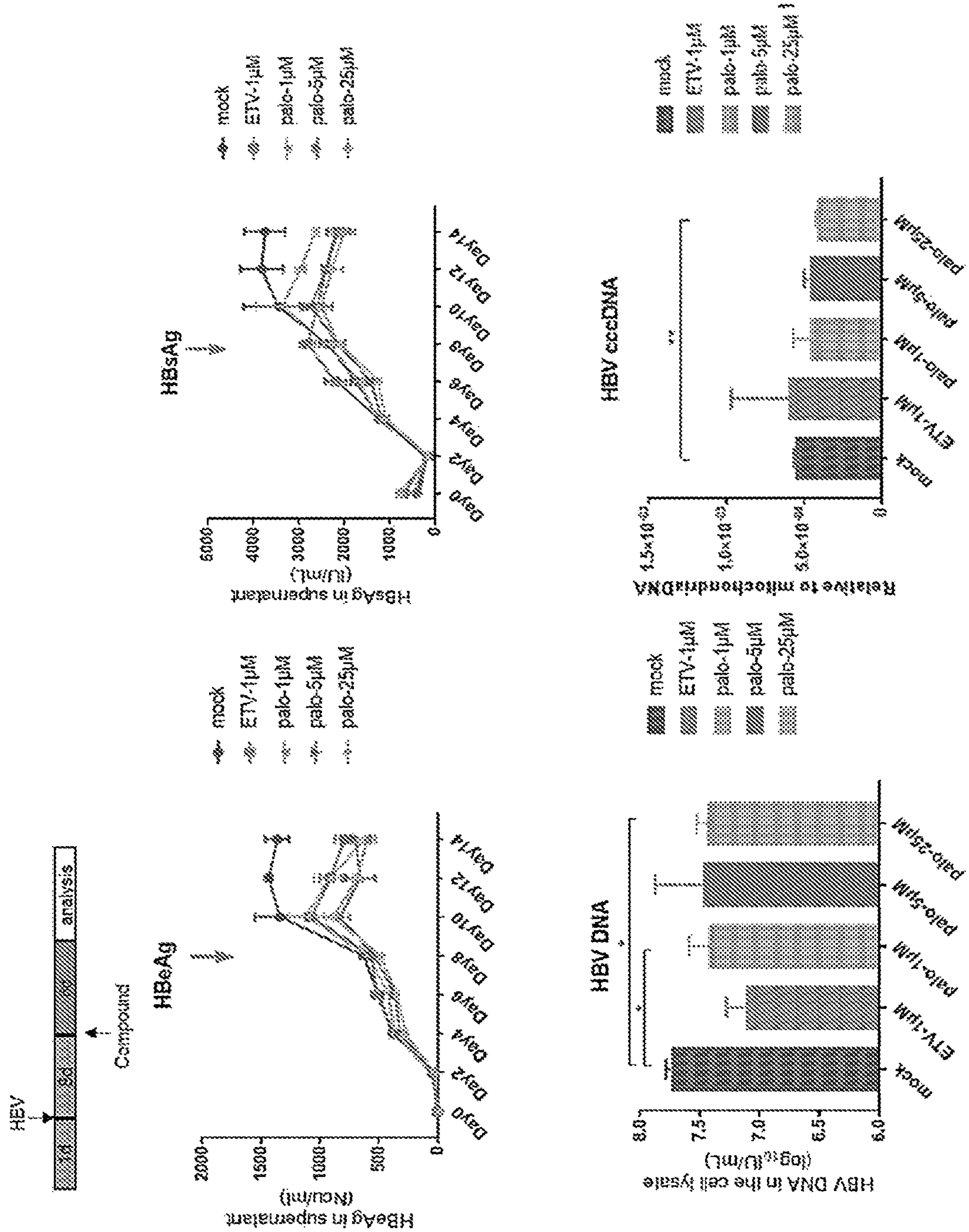
FIG. 7 shows the therapeutic effect of Palovarotene on human primary hepatocytes infected by HBV.

The experimental results were shown in FIG. 7. The results showed that Palovarotene significantly inhibited the levels of HBeAg ($p<0.05$) and HBsAg ($p<0.05$) in the cell supernatant when the drug was added for treatment 8 days after infection, and the inhibitory effects of Palovarotene at 5 μM and 25 μM concentrations were more obvious. At 25 μM concentration, Palovarotene had significant inhibitory effects on HBV cccDNA ($p<0.01$) and HBV DNA ($p<0.05$).

The Palovarotene treatment could significantly inhibit HBV viral replication and e-antigen and surface antigen levels of human primary hepatocytes infected by HBV.

Example 7: Safety Assessment of Drug to be Tested in Hbv In Vitro Cell Model

This experiment was carried out in a 96-well culture plate, with $8\times10^4$ corresponding cells plated in each well, and the corresponding medium volume was 100 μL, in which each drug to be tested in the HepG2-hNTCP 2B1, HepaRG M14A and primary hepatocyte experimental groups had three final concentrations of 1 μM, 5 μM and 25 μM, each drug to be tested in the HepAD38 cell experimental group had two final concentrations of 1 μM and 5 μM (the drug was diluted with the corresponding medium to the final concentrations, specifically please refer to Example 1, Example 2, Example 4 and Example 5), and to the blank group the same volume of culture medium without drug was added. After the cells had grown to a suitable density, drug was added to perform treatment for 6 days, during which, the medium was changed every two days with fresh drug-containing medium.

After the drug treatment, 110 μL of medium containing Beyotime CCK-8 cell activity detection reagent (purchased from Beyotime, Art. No. C0038) (the volume ratio of medium to CCK-8 reagent was 100:10) was used for replacement, the cells were incubated at 37° C. for 30 min, and then all the supernatant was collected for detection of absorbance. The absorbance value was read on PHOMO microplate reader purchased from Zhengzhou Autobio.

Figure 8:
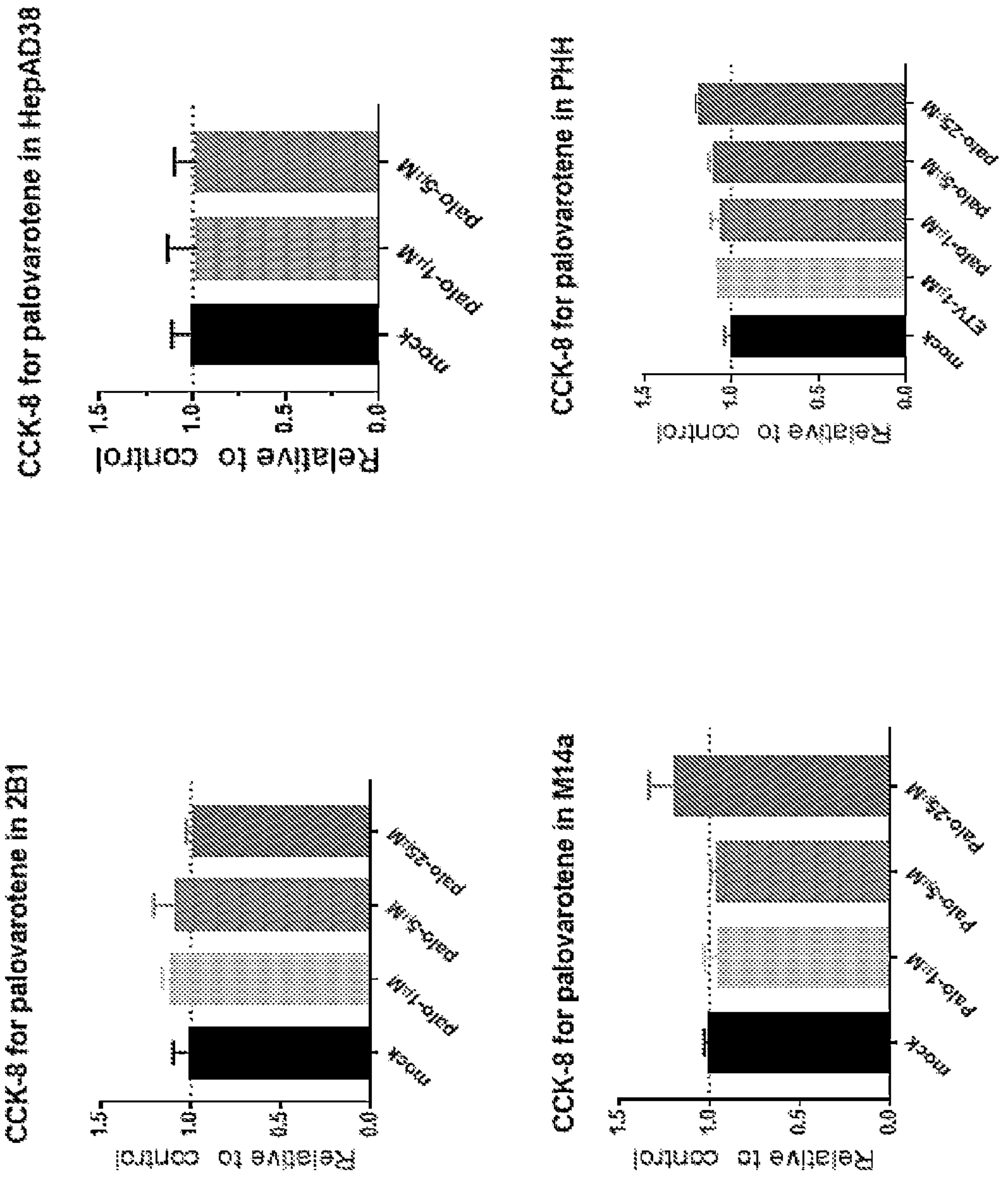
FIG. 8 shows the safety assessment results of Palovarotene in an in vitro cell model.

The results were shown in FIG. 8. The results showed that after HepG2 hNTCP 2B1, HepaRG M14a, HepAD38 and human primary hepatocytes were treated with the drug Palovarotene at concentrations of 1 μM, 5 μM and 25 μM, the CCK-8 absorbance values of each experimental group were not significantly different from that of the blank group, suggesting that the drug had no significant effect on cell activity at these concentrations.

The examples of the present application showed that the compound of Formula I (including Palovarotene) could significantly reduce the levels of HBsAg and HBeAg in cell culture supernatant, and the levels of intracellular HBV DNA and cccDNA in the HBV in vitro research model, in which the treatment with a drug dose of 5 μM could achieve better effect in the antiviral therapy of cells. The drug has the potential to be developed as a therapeutic drug against hepatitis B virus.

Finally, it should be noted that the above examples are only used to illustrate the technical solutions of the present application rather than to limit them; although the present application has been described in detail with reference to the preferred examples, those of ordinary skill in the art should understand: the specific embodiments of the present application may be modified or some technical features may be equivalently replaced; without departing from the spirit of the technical solutions of the present application, all of them should fall within the scope of the technical solutions as claimed in the present application.

What is claimed is:

1. A method for the treatment of a disease or infection caused by HBV or for anti-HBV treatment, comprising:

administering to a subject in need thereof an effective amount of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof,

I

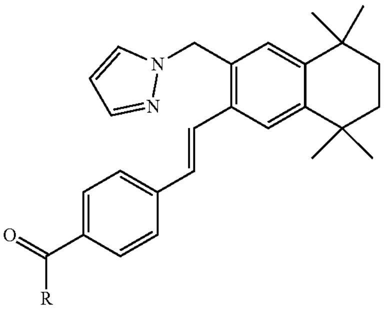

wherein R is hydroxyl, amino, $C_{1-6}$ alkyl-amino-, di($C_{1-6}$ alkyl)-amino-, $C_{1-6}$ alkoxy, $C_{1-6}$ haloalkoxy, $C_{1-6}$ alkyl, $C_{1-6}$ haloalkyl, $C_{3-6}$ cycloalkyl, $C_{3-6}$ cycloalkoxy, phenoxy or benzyloxy.

2. A method for inhibiting the replication or reproduction of HBV in a cell, comprising:

administering to a subject in need thereof an effective amount of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof,

I

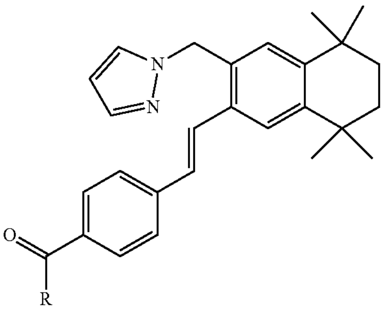

wherein R is hydroxyl, amino, $C_{1-6}$ alkyl-amino-, di($C_{1-6}$ alkyl)-amino-, $C_{1-6}$ alkoxy, $C_{1-6}$ haloalkoxy, $C_{1-6}$ alkyl, $C_{1-6}$ haloalkyl, $C_{3-6}$ cycloalkyl, $C_{3-6}$ cycloalkoxy, phenoxy or benzyloxy.

3. A method for the clearance of HBV in a cell, comprising:

administering to a subject in need thereof an effective amount of a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof or a pharmaceutical composition comprising a compound represented by Formula I, a stereoisomer, a solvate, a pharmaceutically acceptable salt, a hydrate or a solvate of the pharmaceutically acceptable salt, a pharmaceutically acceptable ester, or various pharmaceutically acceptable modifications thereof,

I

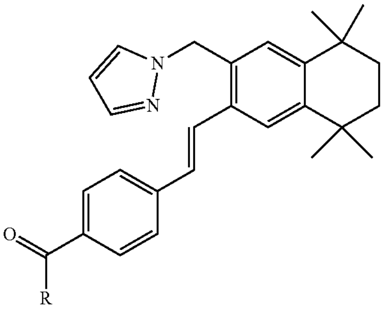

wherein R is hydroxyl, amino, $C_{1-6}$ alkyl-amino-, di($C_{1-6}$ alkyl)-amino-, $C_{1-6}$ alkoxy, $C_{1-6}$ haloalkoxy, $C_{1-6}$ alkyl, $C_{1-6}$ haloalkyl, $C_{3-6}$ cycloalkyl, $C_{3-6}$ cycloalkoxy, phenoxy or benzyloxy.

4. The method according to claim 1, wherein the pharmaceutical composition further comprises a pharmaceutically acceptable carrier or excipient, and the compound, stereoisomer, solvate, pharmaceutically acceptable salt, hydrate or solvate of the pharmaceutically acceptable salt, pharmaceutically acceptable ester, or various pharmaceutically acceptable modifications thereof is present in a therapeutically effective amount.

5. The method according to claim 1, wherein the pharmaceutical composition is a solid preparation, an injection, an external preparation, a spray, a liquid preparation, or a compound preparation.

6. The method according to claim 1, wherein R is hydroxyl, amino, methyl, ethyl, n-propyl, isopropyl, n-butyl, isobutyl, sec-butyl, tert-butyl, $C_5$ straight or branched alkyl, $C_6$ straight or branched alkyl, methoxy, ethoxy, n-propoxy, isopropoxy, n-butoxy, isobutoxy, tert-butoxy, pentyloxy, hexyloxy, methylamino, ethylamino, propylamino, butylamino, dimethylamino, diethylamino, dipropylamino, dibutylamino, cyclopropyl, cyclobutyl, cyclopentyl, cyclohexyl, cyclopropoxy, cyclobutoxy, cyclopentyloxy, cyclohexyloxy, phenoxy, benzyloxy, chloromethyl, chloroethyl, dichloroethyl, trifluoromethyl, difluoromethyl, monofluoromethyl, chloromethoxy, chloroethoxy, dichloroethoxy, trifluoromethoxy, difluoromethoxy or monofluoromethoxy.

7. The method according to claim 1, wherein the disease caused by HBV is viral hepatitis B, or hepatitis B-related cirrhosis or primary liver cancer.

8. The method according to claim 7, wherein the viral hepatitis B is chronic viral hepatitis B, acute viral hepatitis B or chronic active hepatitis.

9. The method according to claim 6, wherein R is hydroxyl.

10. The method according to claim 6, wherein R is amino, methylamino, ethylamino, propylamino, butylamino, dimethylamino, diethylamino, dipropylamino or dibutylamino.

11. The method according to claim 6, wherein R is methoxy, ethoxy, n-propoxy, isopropoxy, n-butoxy, isobutoxy, tert-butoxy, pentyloxy or hexyloxy.

12. The method according to claim 6, wherein R is cyclopropoxy, cyclobutoxy, cyclopentyloxy or cyclohexyloxy.

13. The method according to claim 6, wherein R is phenoxy or benzyloxy.

14. The method according to claim 6, wherein R is methyl, ethyl, n-propyl, isopropyl, n-butyl, isobutyl, sec-butyl, tert-butyl, $C_5$ straight or branched alkyl, or $C_6$ straight or branched alkyl.

15. The method according to claim 6, wherein R is cyclopropyl, cyclobutyl, cyclopentyl or cyclohexyl.

16. The method according to claim 6, wherein R is chloromethyl, chloroethyl, dichloroethyl, trifluoromethyl, difluoromethyl or monofluoromethyl.

17. The method according to claim 6, wherein R is chloromethoxy, chloroethoxy, dichloroethoxy, trifluoromethoxy, difluoromethoxy or monofluoromethoxy.

18. The method according to claim 2, wherein the cell is a cell of mammal.

19. The method according to claim 2, wherein the pharmaceutical composition further comprises a pharmaceutically acceptable carrier or excipient, and the compound, stereoisomer, solvate, pharmaceutically acceptable salt, hydrate or solvate of the pharmaceutically acceptable salt, pharmaceutically acceptable ester, or various pharmaceutically acceptable modifications thereof is present in a therapeutically effective amount.

20. The method according to claim 3, wherein the pharmaceutical composition further comprises a pharmaceutically acceptable carrier or excipient, and the compound, stereoisomer, solvate, pharmaceutically acceptable salt, hydrate or solvate of the pharmaceutically acceptable salt, pharmaceutically acceptable ester, or various pharmaceutically acceptable modifications thereof is present in a therapeutically effective amount.

* * * * *